US006200309B1

(12) United States Patent
Rice et al.

(10) Patent No.: US 6,200,309 B1
(45) Date of Patent: Mar. 13, 2001

(54) PHOTODYNAMIC THERAPY SYSTEM AND METHOD USING A PHASED ARRAY RAMAN LASER AMPLIFIER

(75) Inventors: Robert R. Rice, Chesterfield; Mark S. Zediker, Florrisant, both of MO (US)

(73) Assignee: McDonnell Douglas Corporation, St. Louis, MO (US)

( * ) Notice: Subject to any disclaimer, the term of this patent is extended or adjusted under 35 U.S.C. 154(b) by 0 days.

(21) Appl. No.: 09/107,363

(22) Filed: Jun. 30, 1998

Related U.S. Application Data

(63) Continuation-in-part of application No. 08/800,296, filed on Feb. 13, 1997, now Pat. No. 5,832,006.

(51) Int. Cl.[7] .................................................. A61B 18/18
(52) U.S. Cl. .................................. 606/10; 606/9; 607/89; 372/3
(58) Field of Search ............................ 606/9, 10, 13–16; 607/88–94; 372/3, 6, 18, 19, 20, 21–23, 29–32

(56) References Cited

U.S. PATENT DOCUMENTS

| 4,366,809 | 1/1983 | Clark . | |
|---|---|---|---|
| 4,907,238 | * 3/1990 | Chun et al. | 372/32 |
| 4,926,861 | 5/1990 | Fenyo et al. . | |
| 5,058,117 | 10/1991 | Shoshan et al. . | |
| 5,071,416 | * 12/1991 | Eller et al. | 606/3 |
| 5,130,997 | * 7/1992 | Ortiz et al. | 372/21 |
| 5,136,598 | * 8/1992 | Weller et al. | 372/26 |
| 5,151,909 | * 9/1992 | Davenport et al. | 372/22 |
| 5,222,953 | 6/1993 | Dowlatshahi et al. . | |
| 5,260,954 | 11/1993 | Dane et al. . | |
| 5,265,106 | 11/1993 | Garcia et al. . | |
| 5,453,814 | 9/1995 | Aiyer . | |
| 5,505,726 | * 4/1996 | Meserol | 606/9 |
| 5,616,140 | * 4/1997 | Prescott | 606/10 |
| 5,653,706 | * 8/1997 | Zavislan et al. | 606/9 |
| 5,832,006 | * 11/1998 | Rice et al. | 372/3 |
| 5,847,816 | * 12/1998 | Zediker et al. | 356/5.09 |
| 5,866,898 | * 2/1999 | Hodgson et al. | 250/227.14 |
| 6,052,393 | * 4/2000 | Islam | 372/6 |

OTHER PUBLICATIONS

Sentrayan et al., "Observation of Strong Forward Emission due to UV Multiphoton–Dissociative Excitation of CH4:N2 Mixture", Spectroscopy Letters, 29(3), 401–416 (1996).*
"Phased–array power amplifiers", Microwave Journal, Feb. 1974, vol. 17, (No. 2):28.*
Johannsen, K. G.; Hintze, J. "Intermodulation in Multiple Fixed Beam Distributed Amplifier Phased Array Antenna Systems." International Journal of Satellite Communications, May–Jun. 1991, vol. 9, (No. 3):155–65, 1996.*

* cited by examiner

Primary Examiner—Linda C. M. Dvorak
Assistant Examiner—Ahmed Farah
(74) Attorney, Agent, or Firm—Westerlund & Powell, P.C.; Robert A. Westerlund; Raymond H. J. Powell, Jr.

(57) ABSTRACT

System and method for photodynamic therapy using a phased array Raman laser amplifier including a beam generator for generating a fundamental laser beam and a Raman seed frequency laser beam, and a fiber optic laser amplifier array for forming a diffraction limited output laser beam at the Raman seed frequency by amplifying the fundamental laser beam to a power level corresponding to the Stimulated Raman Scattering (SRS) threshold to thereby pump the SRS process and provide Raman gain to the Raman seed frequency laser beam.

17 Claims, 10 Drawing Sheets

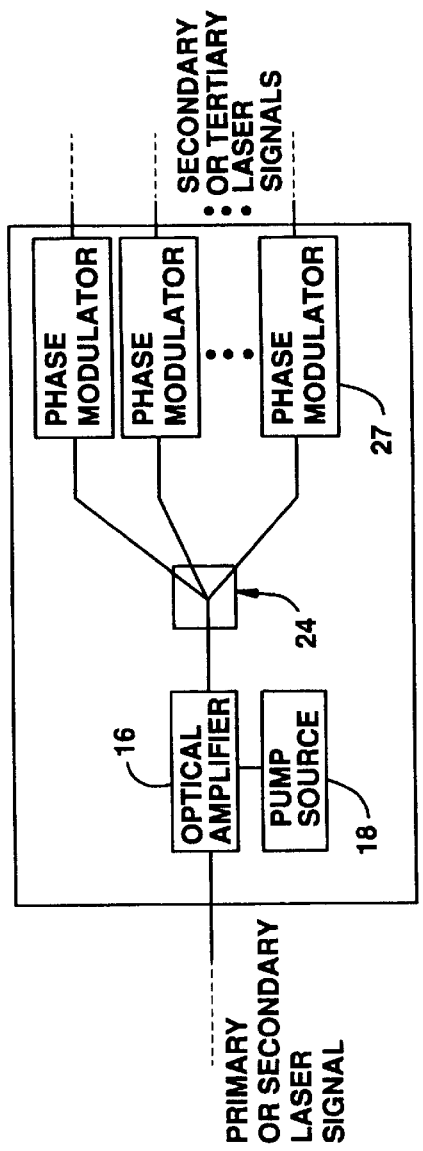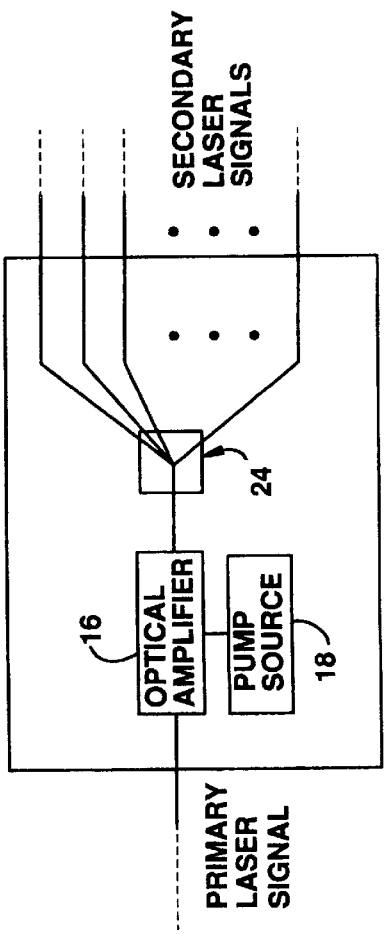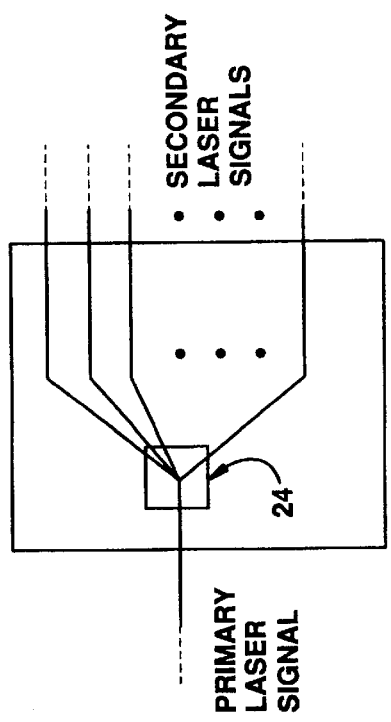

PHOTODYNAMIC THERAPY SYSTEM AND METHOD USING A PHASED ARRAY RAMAN LASER AMPLIFIER

RELATED APPLICATION INFORMATION

This application is a continuation-in-part of U.S. application Ser. No. 08/800,296, filed Feb. 13, 1997, now U.S. Pat. No. 5,832,006, and the entire contents of which, including that of the other applications referenced therein, are incorporated herein by reference for all purposes.

BACKGROUND OF THE INVENTION

The present invention relates generally to photodynamic therapy, and, more particularly to photodynamic therapy using an irradiation source derived from a phased array Raman laser amplifier.

Photodynamic therapy ("PDT") is an emerging modality in which a photosensitizing drug localizes to diseased tissue upon introduction into the body and it then is activated by light of a specific wavelength. The photosensitizers have biolocalization properties and are optically excitable. That is, upon introduction, there is a period of time during which the photosensitizer is absorbed by all cells, but thereafter, the agent rapidly leaves most normal cells while remaining in any tumerous cells in organs and diseased tissues for a longer period of time. The treated cancer cells are then exposed to light from a laser chosen for its ability to activate the photosensitizing agent. Typically, laser light is focused into a beam so it can be aimed at a specific area of the body being treated, and the laser light normally produces a narrow range of light frequencies. It is known in the PDT field that light in the 600–1000 nm spectral region (the "photothera-peutic window") possesses maximum penetration power into most human tissues owing to the low absorptivity of the normal cell constituents in this region and the relatively inefficient scattering of red light by cell organelles. Therefore, red light, in particular, possesses a high penetration power into human tissues and can be selectively absorbed by red-light-absorbing photosensitizing agents (e.g., certain known porphyrins, chlorins, carbocyanines, phthalocyanines, naphthalocyanines, and derivatives thereof) localized in predetermined sites of the organism.

In any event, photosensitizer agents are used in PDT that capture the light energy at the specific wavelength generated by the laser to create an excited state molecule that causes localized tissue destruction in the presence of oxygen without causing damage to the surrounding healthy tissues. Namely, after absorbing the light of the appropriate wavelength, the photosensitizer becomes activated to a higher energy state capable of generating singlet oxygen molecules that react with cellular components to induce cell death, i.e., they have cytotoxic effects. The light exposure must be timed carefully so that it occurs when most of the photosensitizing agent has left healthy cells but is still present in cancerous ones.

There is a great deal of interest in developing PDT in the oncology field because it does not cause the severe side effects of chemotherapy and radiation therapy, such as nausea, diarrhea, hair loss, and organ failure, and it is less invasive than surgical excision in the case of skin surface cancers. Also, PDT can be used in conjunction with, and not to the exclusion of, conventional cancer treatments, such as with cancer drugs or radiation.

For instance, the standard therapy for skin tumors has been surgical excision. However, photodynamic therapy based on the phototoxicity of photosensitizing agents, such as porphyrins which are the natural precursors of hemoglobin, recently have been effectively used for treatment of skin tumors. Topical application of porphyrins followed by tumor exposure to red light (e.g., in the 630–670 nm $\lambda$ range) has been shown to be an effective therapy for several types of tumors, such as for solar keratoses, superficial basal cell carcinomas of the skin and Bowen's disease. Also, the U.S. Food and Drug Administration has approved a photosensitizing agent called dihematoporphyrin ether/ester (DHE), or Photofrin-R™, to relieve symptoms of esophageal cancer that is causing obstruction and for esophageal cancer that cannot be satisfactorily treated with lasers alone.

However, a problem in the PDT field is that no one type of photosensitizer agent can be universally employed for all conceivable PDT treatments due to the physicochemical, photochemical and photophysical peculiarities of any given photosensitizer agent. Also, some currently used photosensitizer agents for PDT are unstable in vivo or induce hyper-photosensitivity in the patient in the case of certain hematoporphyrins and their derivatives used in treatment of skin tumors. This is spurring continuing research into development of a new generation of PDT photosensitizer agents that avoid these drawbacks. Also, the field is interested in developing photosensitizers that can be effectively used in PDT treatments where needed to deeply penetrate tissues to reach the malignant cells, among other things. As a consequence, new types of photosensitizer agents for PDT are being rapidly researched and developed on an ongoing basis.

These different types of photosensitizer agents can and often do require irradiation at vastly different wavelengths relative to one another for achieving excitation. Also, a laser is needed that operates at an appropriate power level to accommodate factors such as penetration depth of the beam into living tissue. To meet this challenge, practioners in the PDT field have previously resorted to case-by-case searches for laser equipment having wavelength and power attributes that match the requirements of the particular photosensitizer agent desired to be tested or used for a given PDT procedure. This can be a time-consuming process even if an acceptable laser-photosensitizer agent match is ultimately made. Moreover, given that each different type of laser equipment represents a relatively expensive piece of hardware, it also can be costly to proceed in this manner where a wide array of photosensitizer agents are expected to be employed.

Consequently, from the above, it can be appreciated that the scope and potential of PDT could be substantially improved if more versatile laser systems could provided that could accommodate the optical requirements of a wide diversity of photosensitizer agents. The operation of a single efficient laser source for PDT treatments in general at different selectable arbitrary wavelengths for the treatment and photosensitive materials at hand would be of enormous advantage. It is Applicants' recognition that what is needed in this regard is a narrow line width, single frequency-selectable solid state laser amplifier that is both compact and efficient.

Furthermore, to understand the backdrop of laser technology to the present invention, some discussion is thought appropriate on the state of Raman shifted solid state laser technology. One laser transmitter in this regard which has high power output characteristics is a Master Oscillator—Phased Power Amplifier Array (MO)-(PPAA) laser system previously disclosed in commonly-assigned, U.S. application Ser. No. 08/782,175, which was filed on Jan. 14, 1997, now U.S. Pat. No. 5,847,816, and which patent is incorporated herein by reference for all purposes.

As illustrated in FIG. 1, the MO-PPAA laser system includes a MO 100 coupled to a fiber optic power amplifier 200. MO 100 is a stable, very narrow line width, laser, which is operating in a $TEM_{00}$ mode at a frequency within the gain spectrum of the power amplifier 200 and which can be coupled by optical fiber to deliver a continuous wave signal to downstream components (not shown).

It will be appreciated that the master oscillator laser 100 can be any conventional master oscillator laser, although the master oscillator is likely a fiber laser oscillator. Some additional conventional components are understood to be part of any practical MO-PPAA laser system and have been omitted. For example, one of ordinary skill in this particular art would appreciate that an optical isolator would be located immediately downstream of the master oscillator 100 to prevent feedback from downstream components, e.g., power amplifier 200, that would induce instability in the master oscillator 100. The details of such components are well known to those skilled in the art and will not be discussed further.

Although a single fiber power amplifier 200 will suffice for some short range applications, a coherent array of optical fiber amplifiers collectively forming the fiber optic power amplifier 200 can be particularly advantageous for those specific applications requiring high output power. One such arrangement of a coherent phased array of fiber optic amplifiers generating high power laser beam is shown in FIG. 1, for example, as needed in long range radar system applications. This particular laser power amplifier is also described in detail in copending, commonly assigned U.S. patent application Ser. No. 08/471,870 and U.S. Pat. No. 5,694,408, which application and patent are also incorporated herein by reference for all purposes.

It will be appreciated that the power splitter, amplifier and phase modulator elements 210 in FIG. 1 may be arranged in various configurations other than the exemplary arrangement illustrated in that Figure. The illustrated fiber optic power amplifier 200 of FIG. 1 includes a first stage composed of a first beam splitter element 210, for splitting a received laser beam into a number N of secondary laser beams. Each of the secondary laser beams is provided to a second beam splitter element 210, which produces a number M of tertiary laser beams from a respective one of the secondary laser beams. Each of the tertiary laser beams is amplified by a respective fiber power amplifier generally denoted 220. It should be mentioned that although two separate stages of beam splitter elements 210 and one amplifier stage 220 are depicted in FIG. 1, the fiber optic power amplifier 200 can have more or less amplification stages. For example, when the first and second beam splitter elements 210 include an optical amplifier 16 pumped by a pump source 18, a beam splitter 24 and, optionally, a number N×M of phase modulators, respectively, a total of three amplification devices are included in the power amplifier 220. See FIG. 2a.

Moreover, alternative configurations are possible. For example, the number of series connected elements 210 can be any number greater than or equal to 2. Moreover, element 210 is not limited to the arrangement illustrated in FIG. 2a. For example, the first stage element 210 need not include either an amplifier 16 or a phase modulator 27 (FIG. 2b); alternatively, the first stage element 210 may include optical amplifier 16 but omit phase modulator 27. Needless to say, additional amplifier stages can also be provided.

It will be noted that the fiber optic power amplifier 200 includes a phase modulator 27 in each optical path. These phase modulators 27 are provided to ensure that all of the N×M laser beams output by power amplifier 200 arrive at the output of the power amplifier 200 with a predetermined phase profile to minimize transmission losses. The power amplifier 200 thus includes a waveform sensor 230 in the output optical path. The waveform sensor 230 produces sensor signals which are provided to phase modulators 27 in element 210 via an adaptive waveform controller 240. Examples of the construction and operation of waveform sensor 230 and waveform controller 240 are provided in above-referenced copending, commonly assigned U.S. patent application Ser. No. 08/471,870, and U.S. Pat. No. 5,694,408.

Thus, in the system depicted in FIG. 1, the master oscillator 100 generates a signal at a low power level that is coupled into an optical fiber. The signal, which must be within the gain band of the rare earth dopant used in the system, is amplified and split among many fiber optic power amplifiers in power amplifier 200. Each stage of the power amplifier 200 amplifies the signal to a high level and delivers it to a summing aperture with appropriate beam forming optics (not shown). The phase of the signal from each beam line is individually controlled to form a diffraction limited beam from the array. The master oscillator 100 defines the wavelength and waveform of the signal amplified and radiated by the MO-PPAA laser system, subject to the wavelength constraints mentioned previously.

Nonlinear optical processes such as Stimulated Brillouin Scattering (SBS) and Stimulated Raman Scattering (SRS) can rob power from a coherently amplified lightwave produced in power amplifier 200. SBS is a narrowband process whereby forward-going light is scattered into a backward-going wave shifted by 11 Ghz, more or less. SRS, however, is a broad band effect whereby energy from the original wave is downshifted by 53 nm, nominally, into another forward-going wave. Both of these processes have a threshold-like behavior whereby, for a given fiber length, above a certain power level, significant energy is extracted from the coherently amplified wave into the scattered wave at a different wavelength. Below this threshold, the nonlinear process is not a problem.

Spectral data of light emitted from an exemplary fiber 40 meters in length is shown in FIG. 3. The maximum coupled Nd:YAG power sent down the fiber was 130 Watts at the peak, which is slightly above the Raman threshold. The spectral line of the unshifted 1.064 mm light is narrowest. The first-order Raman line is downshifted by 53 nm to 1.117 mm, as expected from silica-glass fibers. The Raman light can itself be Raman shifted another 53 nm into a second-order Raman line, which is clearly shown in FIG. 3. It will be appreciated that a weak emission at 1178 nm is also illustrated in FIG. 3.

FIG. 4 illustrates how much light is emitted from this same exemplary fiber at the fundamental and Raman wavelengths as a function of light power coupled into the fiber. The data demonstrate that SRS is a highly nonlinear process. Once the SRS threshold is reached, the fundamental light power is virtually clamped and the excess power is shifted to the Raman wavelength. It will be appreciated that the Raman light is self aperturing; it can only be generated in, not outside, the core.

The SRS threshold for the exemplary 40 meter piece of optical fiber discussed above is approximately 100 Watts. It should be pointed out that the SRS process is highly non-linear and thus very sensitive to small variations in parameters such as the mode size, fiber length and core dopants.

Since the SRS is highly dependent on these parameters, it is feasible to increase the SRS threshold by increasing the mode diameter, and vice versa. Simulations show that small changes can result in significant increases or decreases in the SRS gain.

The SRS effect can best be understood by considering the laser pulse shapes and shapes of pulses transmitted through the fiber. The top trace of FIG. 6 depicts the shape of the pulse coming directly from a Nd:YAG laser without propagating through the fiber. The output pulse is approximately 100 ms long with a peak power of 500 watts with a brief burst of relaxation oscillations on the leading edge, chosen to simulate quasi-CW conditions in the fiber. The bottom three traces in FIG. 6 are the shapes of light pulses emitted from the fiber. The peak input power of 130 Watts is shown in the first trace, and the lower traces illustrate the temporal shapes of the 1.064 mm light, the 1st order Raman line and the 2nd order Raman line. Due to the highly nonlinear SRS process, small amplitude variations in the coupled light lead to large variations in the fundamental and Raman light components emitted from the optical fiber.

The fundamental-wavelength pulse with its flat top demonstrates the sharp threshold behavior described previously with respect to FIG. 5. Once the threshold is exceeded, additional coupled power is diverted from the fundamental wavelength into the Raman line. Adding the fundamental and 1st order Raman pulses together (note the waveform amplitude scaling) would result in a waveform similar to that of the original laser pulse in the top trace, consistent with the idea that most of the pulse energy is concentrated at the fundamental and 1st Raman wavelengths. The 2nd order Raman line at the 130 Watt peak power level is very small and flickers on and off from pulse to pulse. Its energy is insignificant compared to that at the other two wavelengths at this incident power level.

It should be pointed out that the SRS gain observed is for a high power signal propagating the entire length of the optical fiber. This is not the case for a high power optical amplifier where a 1.06 mm signal is normally injected at a low level and it will gain power over the entire length of the optical amplifier. This gain of the 1.06 mm signal will effectively decrease the total Raman gain available because of the significantly decreased interaction length. Consequently, achieving 100 Watts CW from an optical amplifier will not be limited by SRS.

As discussed above, the nominal Raman shift is about 53 nm. In other instances, the gain coefficient for the Stimulated Raman Scattering in silica fibers peaks at approximately 40 nm from the original signal, as shown in FIG. 6. It will be appreciated that the Raman gain spectrum actually mirrors the LO phonon spectrum in the fiber core, which depends upon the composition of the glass used to form the core. It will also be appreciated that the first-order Raman line depicted in FIG. 3 is considerably broader than the fundamental line at 1.064 mm because of the broad Raman gain spectrum of silica glass shown in FIG. 6.

SRS occurs all along the optical fiber and it is characterized by a differential scattering cross section, which section is integrated over the solid angle of the numerical aperture of the fiber to determine the probability of a spontaneous Raman photon being captured by the fiber and creating the SRS wave. When SRS is present in the fiber or the potential for SRS is present, the power in the signal wave must be increased rapidly so that energy conversion occurs over as short of a fiber length as physically possible. As the high power propagates along the fiber, the Stokes wave begins to grow. If the desired signal power can be reached before the Stokes wave reaches threshold, then the high power fiber amplifier will operate efficiently. It will be appreciated that the Stokes wave threshold is the point at which the gain in the Stokes wave exceeds the distributed losses in the fiber. Consequently, by designing the fiber amplifier to have a distributed loss at the Stokes wavelength, it is possible to completely suppress the generation of the Stokes wave over relatively long fiber lengths.

To see the effect of the build-up of Raman parasitics see FIGS. 7 and 8. In FIG. 7, a properly designed fiber amplifier pumped from both ends can amplify an input signal to the 100 watt level. In FIG. 8, a longer fiber, again pumped from both ends, allows the onset of parasitic Raman amplification gain, which depletes the signal power and converts it to the down-shifted Raman wavelength.

The master oscillator 100 signal is efficiently amplified by the array 200 of high power fiber optic amplifiers illustrated in FIG. 1 if no parasitic SRS occurs in the high power stages. This is assured by design of these amplifier stages. First, since the Raman gain is a function of the signal amplitude, the diameter of the fiber core can be increased within limits to reduce the intensity at a given signal power level. The limitation here is that the fiber should remain essentially single mode. Second, since the onset of the parasitic Raman signal is rather abrupt and depends on the level of down shifted Raman signal present, a Raman filter can be inserted between the tandem stages of each power amplifier line to impede the build up of the Raman signal. Thus in a prior art system, the Raman signal is a detrimental complication that must be controlled by design.

It will be appreciated that the MO-PPAA illustrated in FIG. 1 consists of a phased array of high power fiber optic amplifiers that amplify a signal within the gain band of the rare earth dopant used in the fiber amplifier core. This restricts the useful band of wavelengths to a few tens of nanometers for each of the limited number of rare earth dopants. Even though the output of such an array can be frequency doubled efficiently, the wavelength restriction mentioned immediately above applies equally to the possible harmonic wavelengths. Therefore, for PDT implementations, the FIG. 1 arrangement would be inadequate. More preferably, the postulated laser amplifier would have an output wavelength which is selectable over a range of hundreds of nanometers above the gain band of the rare earth dopant used in the fiber amplifier core of the laser device.

Based on the above and foregoing, it can be appreciated that there presently exists a need in the practice of the photodynamic therapy art for a laser system which overcomes the above-described deficiencies. The present invention was motivated by a desire to overcome the drawbacks and shortcomings of the presently available technology, and thereby fulfill this need in the art.

SUMMARY OF THE INVENTION

The present invention relates to a system and it method of use for photodynamic therapy ("PDT") permitting for a more widespread application of PDT for tumor eradication or palliation, and the treatment of a variety of other diseases.

In one embodiment of this invention, there is a photodynamic therapy system for irradiating tumor cells in tissue in the presence of a photosensitizer compound with a laser beam at a light wavelength effective to excite the photosensitizer compound to cause cytotoxic effects upon the tumor cells, involving:

light output generating means having a phased array Raman laser amplifier including:
a light beam generator generating a fundamental laser beam and a Raman seed frequency laser beam, and
a laser amplifier array forming a diffraction limited output laser beam at the Raman seed frequency by amplifying the fundamental laser beam to a power level corresponding to a Stimulated Raman Scattering (SRS) threshold to thereby pump the SRS process and provide Raman gain to the Raman seed frequency laser beam; and
means for transmitting the light output to the tissue for treatment purposes. The light output means preferably is a red light output means.

In another embodiment of this invention, there is a method of photodynamic therapy, involving the steps of:
contacting tumor cells with a photosensitizer compound;
irradiating the tumor cells in the presence of the photosensitizer compound with a laser beam at a light wavelength effective to excite the photosensitizer compound to cause cytotoxic effects upon the tumor cells, wherein said laser beam is generated using the aforesaid phased array Raman laser amplifier.

The present invention encompasses a wide variety of PDT treatments using a light irradiation source that generates a high laser power at very precise wavelengths with high efficiency and near diffraction limited output beam quality. Important benefits of the invention are the generation of a high power laser beam for PDT at an arbitrary wavelength with high efficiency while maintaining overall excellent beam quality. The same system architecture will serve to produce an expansive range of output powers over a wide range of wavelengths with only minor architectural variations. A laser amplifier is used in PDT therapy according to this invention whose output wavelength is freely selectable over a range of hundreds of nanometers above the gain band of the rare earth dopant used in the fiber amplifier core. In an exemplary case, each of the optical fiber sections includes a Yb:Er core. In an exemplary case, each of the optical fiber sections includes a Nd doped core.

These and other objects, features and advantages of the invention are disclosed in or will be apparent from the following description of preferred embodiments.

BRIEF DESCRIPTION OF THE DRAWINGS

These and various other features and aspects of the present invention will be readily understood with reference to the following detailed description taken in conjunction with the accompanying drawings, in which like or similar numbers are used throughout, and in which:

FIGS. 2a through 2c illustrate alternative preferred configurations of the selected optical elements within the fiber optic power amplifier as illustrated in FIG. 1;

DETAILED DESCRIPTION OF THE PREFERRED EMBODIMENTS

Figure 1:
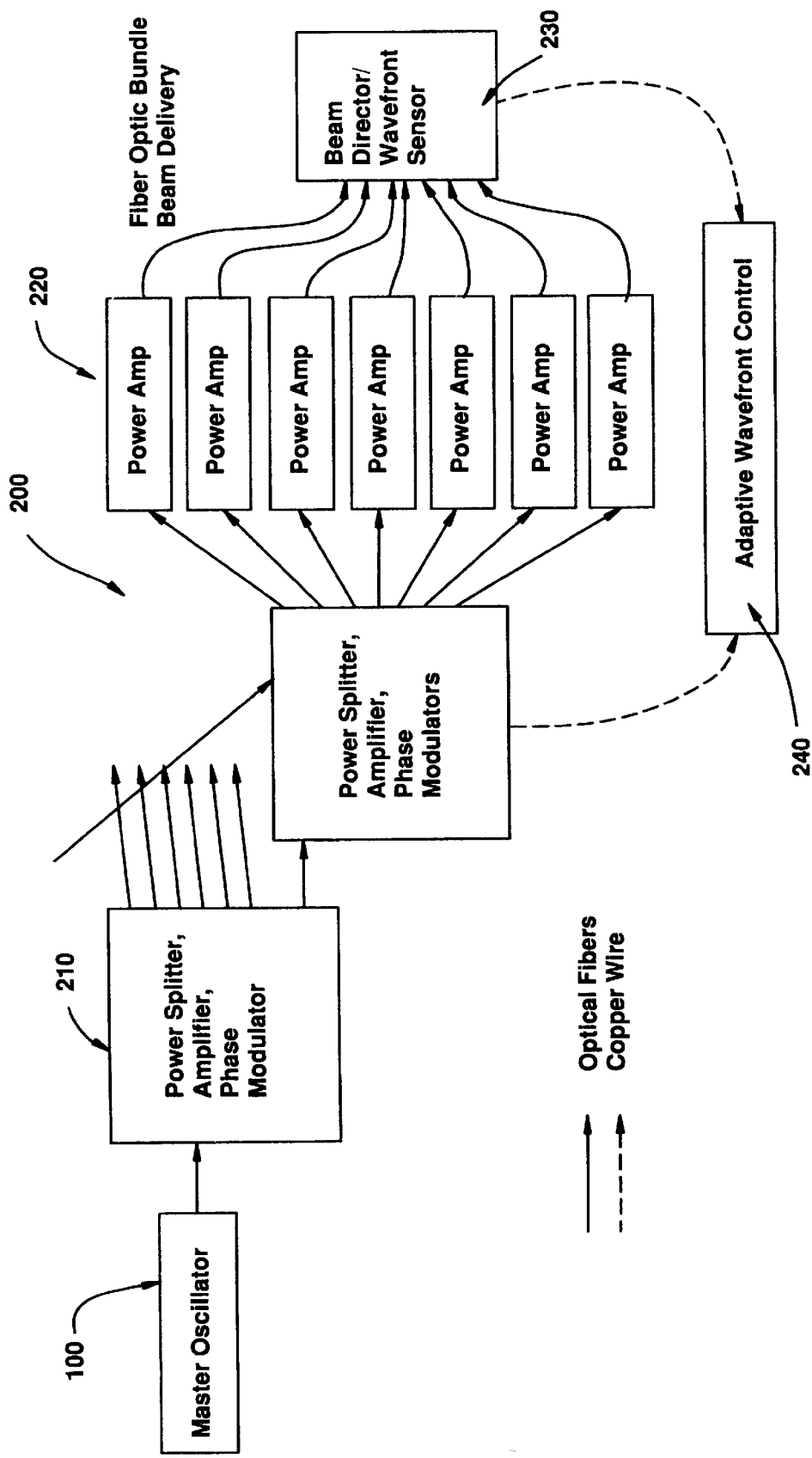
FIG. 1 is a high level block diagram of selected components of a previously proposed fiber optic amplifier.

The important medical application of interest herein involves the ability, as provided by the present invention, to produce precise wavelengths for exciting specific dyes used in photodynamic therapy, for which specifically "tuned" dyes are effective against specific tumors. The present invention can produce a wide range of high power red, blue, and green wavelengths appropriate for a wide variety of conceivable PDT treatments. The laser system used in the present invention permits coverage of the entire spectral region (i.e., the "phototherapeutic window") of greatest significance to the PDT field ranging from about 600 to about 1000 nm. More generally, the laser system used in the present invention permits coverage of wavelengths ranging from about 500 nm to about 1600 nm, and even some wavelength values beyond 1600 nm. In the implementation of the present invention, an operator, viz., a medical doctor or technician, can set the laser equipment via a control panel to "select" the wavelength needed to be generated by the laser equipment that will match the given excitation wavelength parameter of a given photosensitizer to be used in a given PDT treatment.

Advantageously, the tunable output of the laser beam generated by the present invention could be used to pump a variety of solid state lasers with absorption bands in the red light spectral range in particular. That is, coverage in the present invention of the red light spectral range is very important because red light possesses a high penetration power into human tissues and red light can be selectively absorbed by many known classes of photosensitizing agents (e.g. porphyrins, chlorins, phthalocyanines, naphthalocyanines, carbocyanines, and derivatives and analogs thereof, and the like) as localized in predetermined sites of an organism.

The PDT treatment begins by administration of the photosensitizer agent as drugs applied either on the skin to penetrate through to the targeted diseased tissue, or they are injected (e.g., intravenously) into the blood stream, from which the intended area of tissue then absorbs and accumulates the drug. In general, healthy tissues eliminate the photosensitizer agents used in PDT relatively rapidly while they are retained in malignant cell areas for longer periods of time. Medical practioneers and researchers in the PDT field understand that the irradiation of the photosensitized tissue areas must be accomplished in the window of time in which the photosensitizer agent is essentially eliminated from the healthy tissues yet is still concentrated in the target tissues that are in need of treatment. This window of time for effecting the irradiation can vary between different photosensitizer compounds, as different compounds can have different bioabsorption rates, stabilities, and elimination rates, and the time can vary as a function of the PDT treatment location in the body, and so forth, as will be appreciated by persons of skill in the field. Predetermined guidelines and protocol for the timing of the irradiation step will often be available in advance for a given photosensitizer agent and specific PDT treatment, or they can be determined empirically for any given set of PDT conditions.

Figure 10:
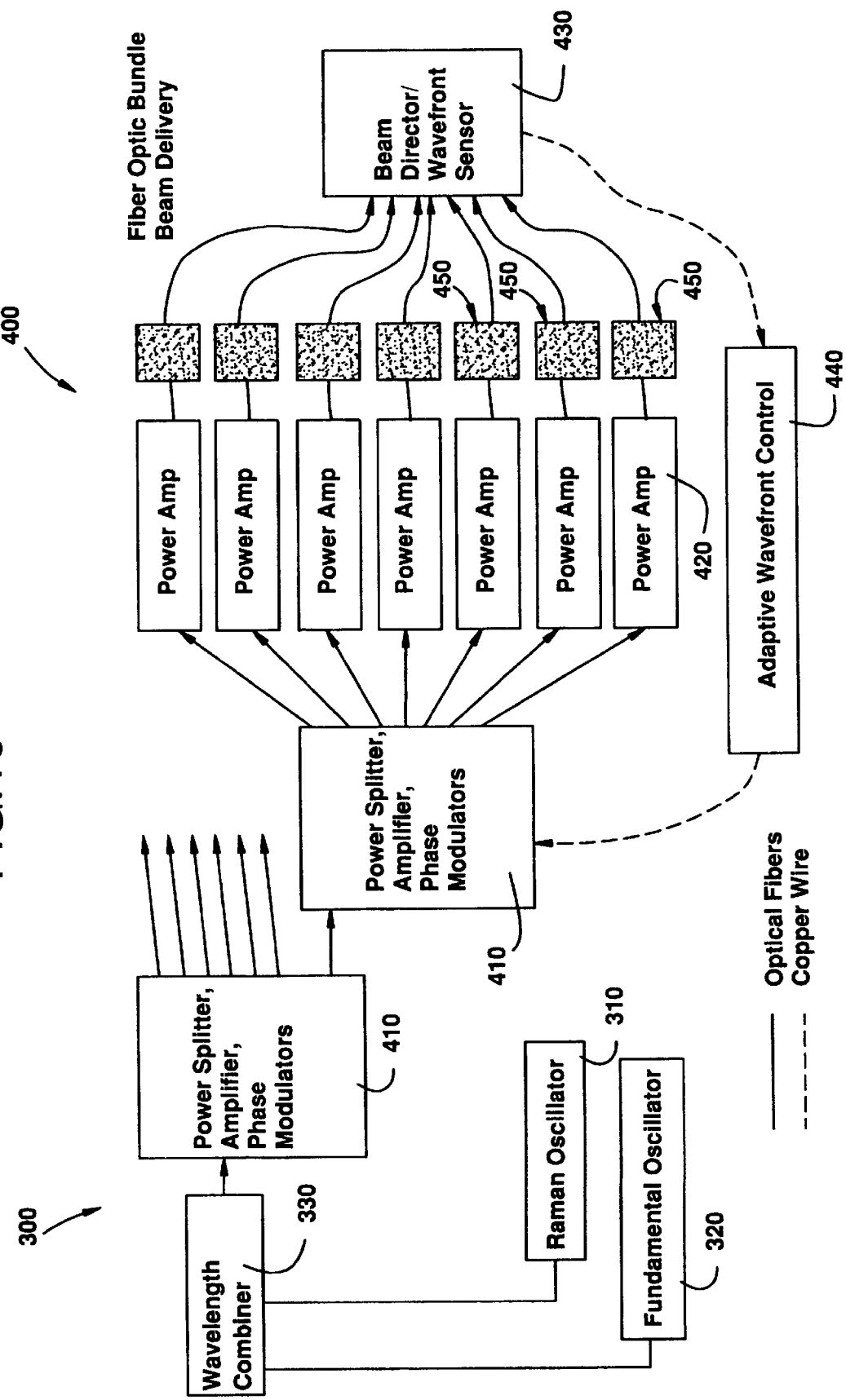
FIG. 10 is a high level block diagram of an alternative phased array Raman laser amplifier according to the present invention.
Figure 11:
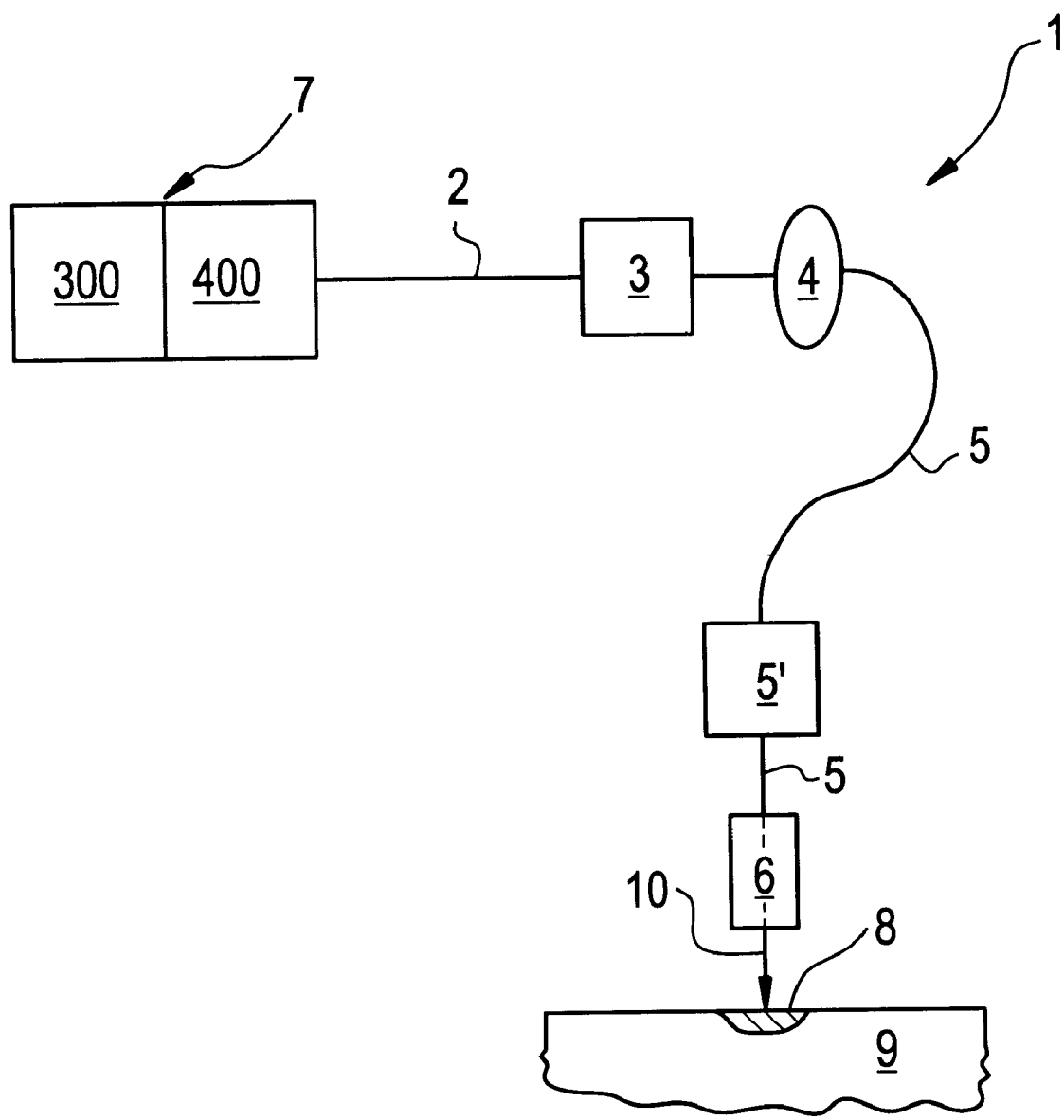
FIG. 11 is a schematical view of a laser light source and delivery system for use in a PDT treatment according to the present invention.

Referring now to the drawings, and, more particularly to FIG. 11, a laser beam generating means 7 is shown constituted by a laser source generator 300 in combination with a Raman amplifier array 400, which features are described in greater detail below in connection with FIGS. 9 and 10. Once the light beam 2 of the desired wavelength is emitted by the laser system 7, it must be transmitted in a satisfactory and convenient manner to a body location where tumor treatment is desired. Although many alternatives in this regard present themselves, the following are preferred. An external shutter 3 to the laser device 7 can be provided to controllably block or permit passage of the light beam while being generated by the laser system 7, or alternatively, feature 3 alternatively can be a modulator that can regulate the intensity of the transmitted light. Optical coupler 4 transmits the light beam to optical fiber transmission systems leading to the tissue to be treated. In this regard, optical fiber lines 5 and block 5'(generally representing all other necessary intervening couplers and optical fiber, and so forth), together constitute a fiber optical fiber delivery system (5, 5') required for transmission of the laser beam 2 from optical coupler 4 to a treatment probe 6. The fiber optical fiber delivery system (5, 5') should be flexible and manually movable. Preferably, the treatment probe 6 is small enough to be a hand-held, manipulatable instrument that holds a terminal end of optical fiber conducting the laser energy. The probe 6 permits an operator to readily direct the light beam onto or into the malignant tissues to be treated.

For example, in PDT treatment of tumors located on or just below the skin surface or on the lining of internal organs, the treatment probe 6 can take the form a small rigid tubular structure housing the terminal end of an optical fiber that transmits the laser energy out of the distal end of the probe. The probe 6 can be brought physically into close proximity to or in direct contact with the malignant tissue area 8 containing pre-absorbed photosensitizer agent (not shown) on the skin surface 9 to be treated with the operator appropriately moving the probe to align the laser beam emitted out of the end face of the probe 6 with the targeted tissue site. Hand-held laser-light directing probes are well-known and widely available for medical uses, and they are generally applicable to implementing the present invention.

Alternatively, the probe 6 can take the form of an optical needle that permits its in vivo insertion through healthy tissues in order to reach a tumor or its insertion within a tumorous tissue mass per se. This modality is relevant to PDT treatment of tumors located further below the skin or within an organ. In this regard, an exemplary optical needle involves an insertable syringe-like needle including a fiber optic core, such as the types described in U.S. Pat. No. 4,336,809, which teachings are incorporated herein by reference. The type of PDT treatment to be practiced will largely govern whether the treatment probe 6 takes the form of an external or internal probe as described above. Conventional optical coupler means can be used to permit quick attachment and replacement of different types of probes, as needed.

The preferred laser light source used in practicing this invention will now be described with reference to FIG. 9, wherein a phased array Raman laser amplifier includes a laser source generator 300, a Raman amplifier array 400 and a frequency doubler 500. As will appreciated from the discussion which follows, although the phased array Raman laser amplifier used in the present invention appears to be similar to that employed in a proposed phased array laser amplifier illustrated in FIG. 1, at first glance, the operation of the phased array laser amplifiers illustrated in FIGS. 1 and 9 are markedly different. In the FIG. 1 system, Stimulated Raman Scattering (SRS) is considered an undesirable parasitic effect that must be controlled to avoid loss of output signal. In contrast, the laser system used in the present invention advantageously employs Stimulated Raman Scattering (SRS) to effect a conversion of the fundamental wavelength of the fiber amplifier array, i.e., of the rare earth dopant used, to the desired operating wavelength matching the excitation wavelength of the particular photosensitizer agent being used in the PDT treatment by one or more Raman scattering steps.

While fiber optic Raman lasers and amplifiers are not new, their use in a high power coherent phased array has not heretofore been suggested, much less as implemented in a PDT treatment. Moreover, inasmuch as a Raman amplifier used according to the present invention is novel, the combination of the Raman amplifier array with a known frequency doubler, either within the final power amplifier stage or downstream of the final power amplifier stage, has never before been suggested or proposed in any context, much less as implemented in a PDT treatment.

Advantageously, the laser source generator 300 includes at least one Raman generator 310 for generating at least one laser beam at the Raman seed frequency, a fundamental oscillator 320 for generating a fundamental laser beam having a frequency corresponding to the gain frequency of the rare earth doped optical fibers employed in the array 400, and a wavelength combiner 330, for combining the Raman seed frequency laser beam and the fundamental laser beam for application to the array 400. It should be mentioned that the wavelength combiner 330 advantageously can be either an active or passive device; most preferably, the wavelength combiner 330 is a member of the class of devices generally denoted a wavelength division multiplexer (WDM).

Preferably, the Raman generator 310 generates at least one Raman seed frequency laser beam, i.e., a laser beam having an output wavelength approximately equal to the desired output laser beam. It should be mentioned that laser beams at intermediate Raman shifted wavelengths advantageously can be provided by the Raman generator 310. By way of example, for a PDT application for treatment of basal cell carcinomas using a hematoporphyrin ether/ester (DHE, such as Photofrin™), as the photosensitizer, the desired output laser beam has about a 626 nm wavelength. An exemplary silica glass optical fiber produces a Raman down shift, often referred to as a Stokes shift, of 53 nm, nominally. A first order Raman laser beam at a first wavelength and a second order Raman laser beam at a higher second wavelength are generated by Raman generator 310 and provided to array 400. As a practical matter, the second order Raman laser beam, i.e., the Raman seed frequency laser beam, will be locked to the wavelength of the desired output laser beam, i.e., 626 nm, for the example indicated. Advantageously, since the output of the fundamental oscillator 320 is selectable over a range measured in tens of nanometers, a 520 nm fundamental laser beam can be coupled to the array 400 via the wavelength combiner 330 such that the difference between the wavelengths of the fundamental laser beam and the desired output laser beam is 106 nm±10 nm, i.e., two Raman shifts for the exemplary optical fiber.

Figure 9:
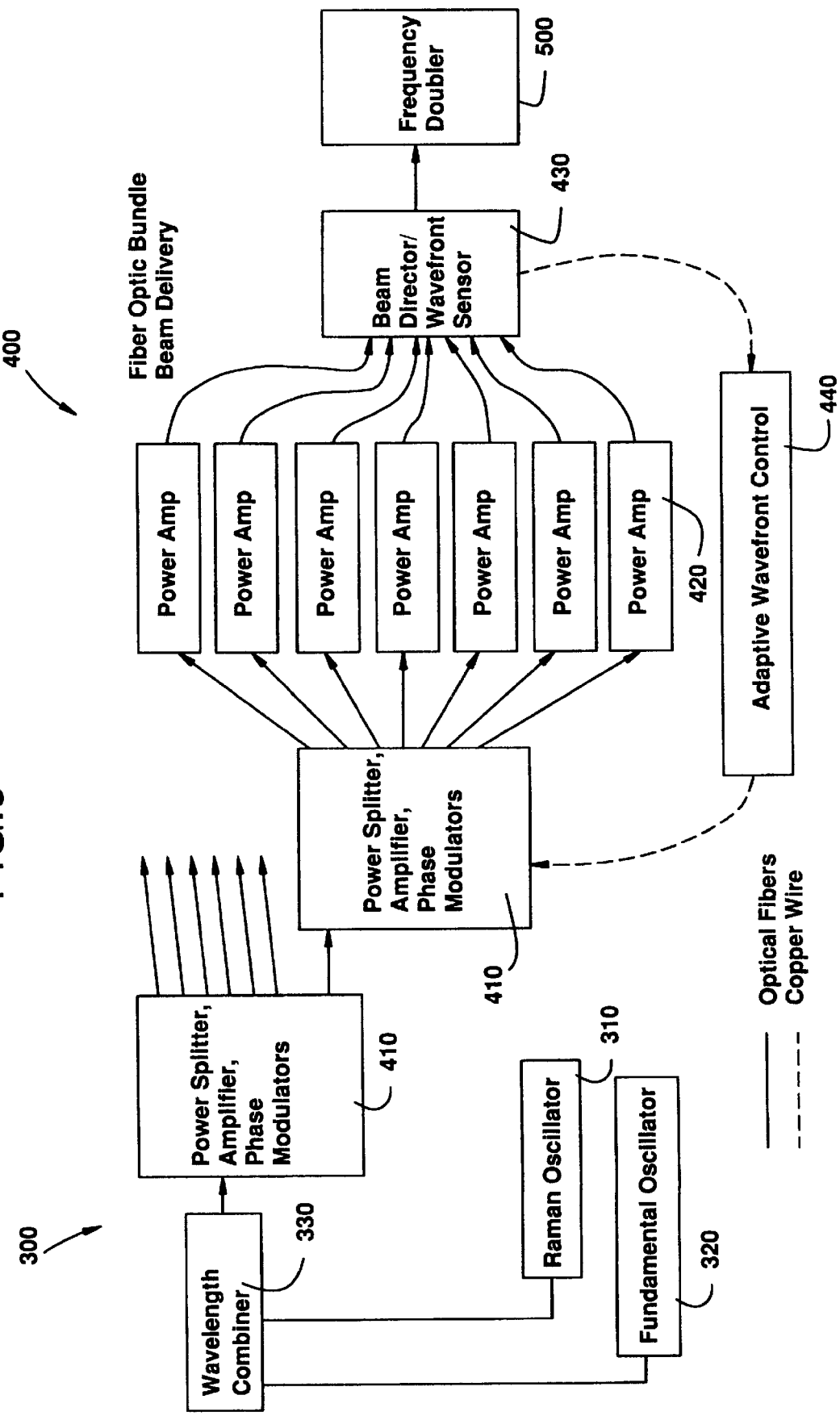
FIG. 9 is a high level block diagram of a phased array Raman laser amplifier according to the percent invention.

Still referring to FIG. 9, it will be appreciated that the power splitter, amplifier and phase modulator elements 410 may be arranged in various configurations other than the exemplary arrangement illustrated in that Figure. The illustrated fiber optic power amplifier 400 of FIG. 9 includes a first stage composed of a first beam splitter element 410, for splitting a received laser beam into a number N of secondary laser beams. Each of the secondary laser beams is provided to a second beam splitter element 410, which produces a number M of tertiary laser beams from a respective one of the secondary laser beams. Each of the tertiary laser beams is amplified by a respective fiber power amplifier generally denoted 420. It should be mentioned that although two separate stages of beam splitter elements 410 and one amplifier stage 420 are depicted in FIG. 9, the fiber optic power amplifier 400 according to the present invention beneficially can have more or less amplification stages. For example, when the first and second beam splitter elements 420 include an optical amplifier 16 pumped by a pump source 18, a beam splitter 24 and, optionally, a number N×M phase modulators, respectively, a total of three amplification devices are included in the power amplifier 400. See FIG. 2a.

Preferably, the fundamental laser beam at the fundamental wavelength is injected into the input port of the array 400 as shown, and the fundamental laser beam is amplified in each fiber beam line to a level sufficient to pump the SRS process in the power amplifier stage 420, which in turn provides Raman gain for the Raman signal to be amplified. As mentioned previously, the desired laser beam to be amplified at the Raman wavelength is simultaneously injected into the phased array input port through the wavelength combiner 330 as shown.

Advantageously, the desired output laser beam at the Raman wavelength is sensed by beam director/wavefront sensor 430 so that the phase of each beam line beneficially can be adjusted electronically using the adaptive wavefront controller 440 to form a diffraction limited beam. It will be appreciated that the same control system and beam forming algorithms used to form a fundamental wavelength beam in FIG. 1 can be used to form the Raman wavelength beam in the phased array Raman laser amplifier illustrated in FIG. 9. Advantageously, the desired output laser beam can be frequency doubled either by a single nonlinear crystal 500 depicted in FIG. 9, or by an array of nonlinear crystals, generally denoted 450, located immediately downstream of the power amplifiers 420. It will be appreciated that the configuration of FIG. 10 is advantageous for very high average power applications.

It should be mentioned that various filters such as a notch filter advantageously can be used to ensure that the desired output laser beam is effectively separated from the lower power fundamental and first order Raman laser beams produced by the power amplifiers 420. Since the frequency doubler 500 is itself a nonlinear device adapted to the desired output laser beam, filtering of the desired output laser beam advantageously can be omitted.

As discussed above, the desired wavelength to be amplified can be generated with high precision but low efficiency at a low power. For applications that involve atomic resonance, the frequency can be actively locked using an appropriate absorption cell. Preferably, active locking is performed in the Raman oscillator 310 such the Raman laser beam wavelength is an integer multiple of the wavelength of the desired output laser beam. This is true also if the signal is at a harmonic wavelength.

Moreover, as previously discussed, more than one Raman (Stokes) down shift may be required to achieve the desired wavelength; in this case, multiple Raman wavelengths advantageously can be injected into the phased array 400. Thus, the first Stokes wavelength depletes the fundamental wavelength in the fiber, the second Stokes wavelength depletes the first Stokes wavelength as it builds up in the fiber, and so on to the desired wavelength to be amplified. It should also be mentioned that once the desired Stokes wavelength builds up in the fibers of the power amplifiers 420 precautions must be taken to prevent further Raman shifts, as noted previously, by design or filtering.

While the present invention was discussed with respect to a single optical fiber type, the present invention is not limited to a single optical fiber type or even an amplifier array utilizing optical fibers. The present invention works for any rare earth dopant; Raman shifts from starting wavelengths such as 2.05 mm or longer would enable high power mid-infrared sources. Advantageously, the rare earth doped optical fiber can be fabricated using Nd, Yb, Yb:Er, Er, Pr, and Ho, or combinations thereof, as the dopant. Moreover, it will be appreciated that the present invention is not limited to arrays of rare earth doped optical fibers; semiconductor arrays advantageously can be used where minimal output power and maximum bandwidth are the essential design constraints.

It will be appreciated that a single beam line Raman shifted amplifier, which is prior art, is both similar to and fundamentally different from a phased array of such devices. For example while both could be used to produce a precise frequency, for example, as required to excite photosensitizer dyes in the PDT application, the capability to scale-up the output power to the level likely to be needed, or to any arbitrary level, would be lacking in the single beam line Raman shifted amplifier since there are real limitations on the capability of single mode fibers to transmit power. An array of fiber amplifiers allows scaling-up by combining additional fiber amplifiers coherently. Moreover, the active beam sensing and control system provided by elements 430 and 440 of the power amplifier array 400 achieves a diffraction limited output for an arbitrary number of fibers, i.e., any number of power amplifiers 420.

Likewise, were it possible to generate an arbitrary power level from a single, prior art Raman fiber amplifier, it would not be possible to frequency double an arbitrarily high power using physically realizable nonlinear crystals. Hence, the possibility of using an array of nonlinear crystals in a phased coherent array frequency doubler allows generation of a diffraction limited second harmonic beam at an arbitrarily high power.

Figure 3:
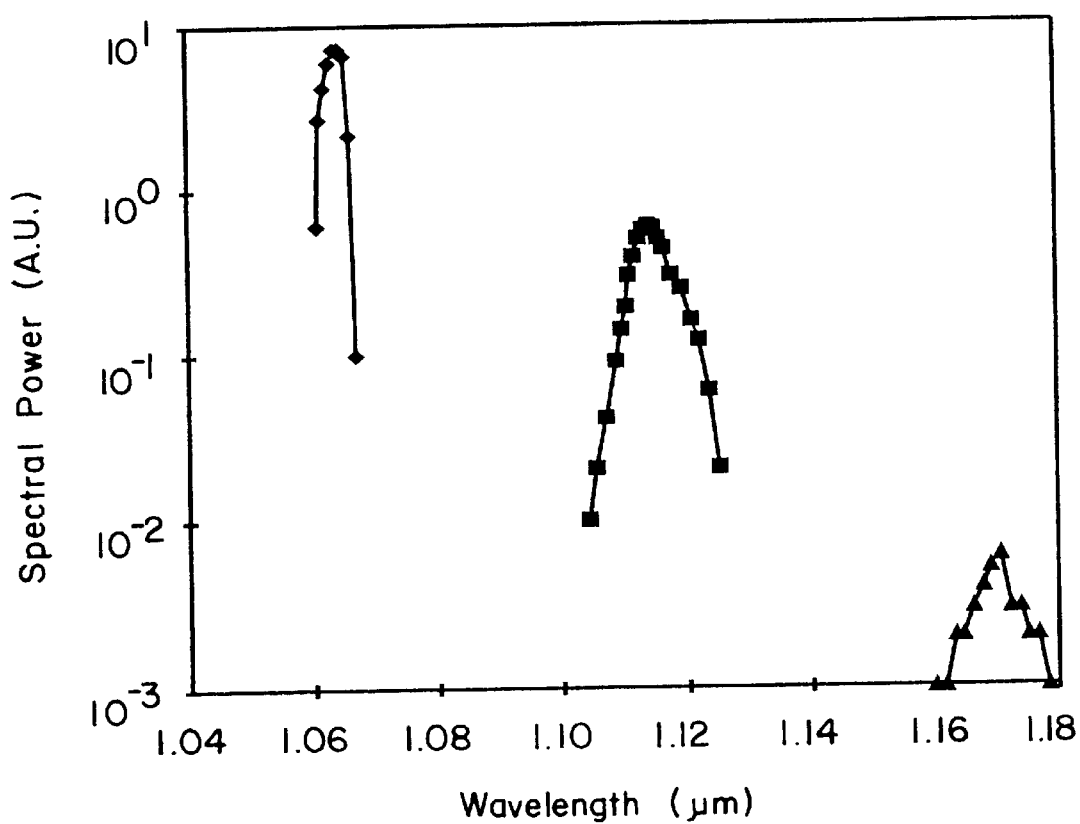
FIG. 3 is a series of curves depicting spatial power distribution with respect to wave length in an optical fiber operating above the Stimulated Raman Scattering (SRS) threshold.
Figure 4:
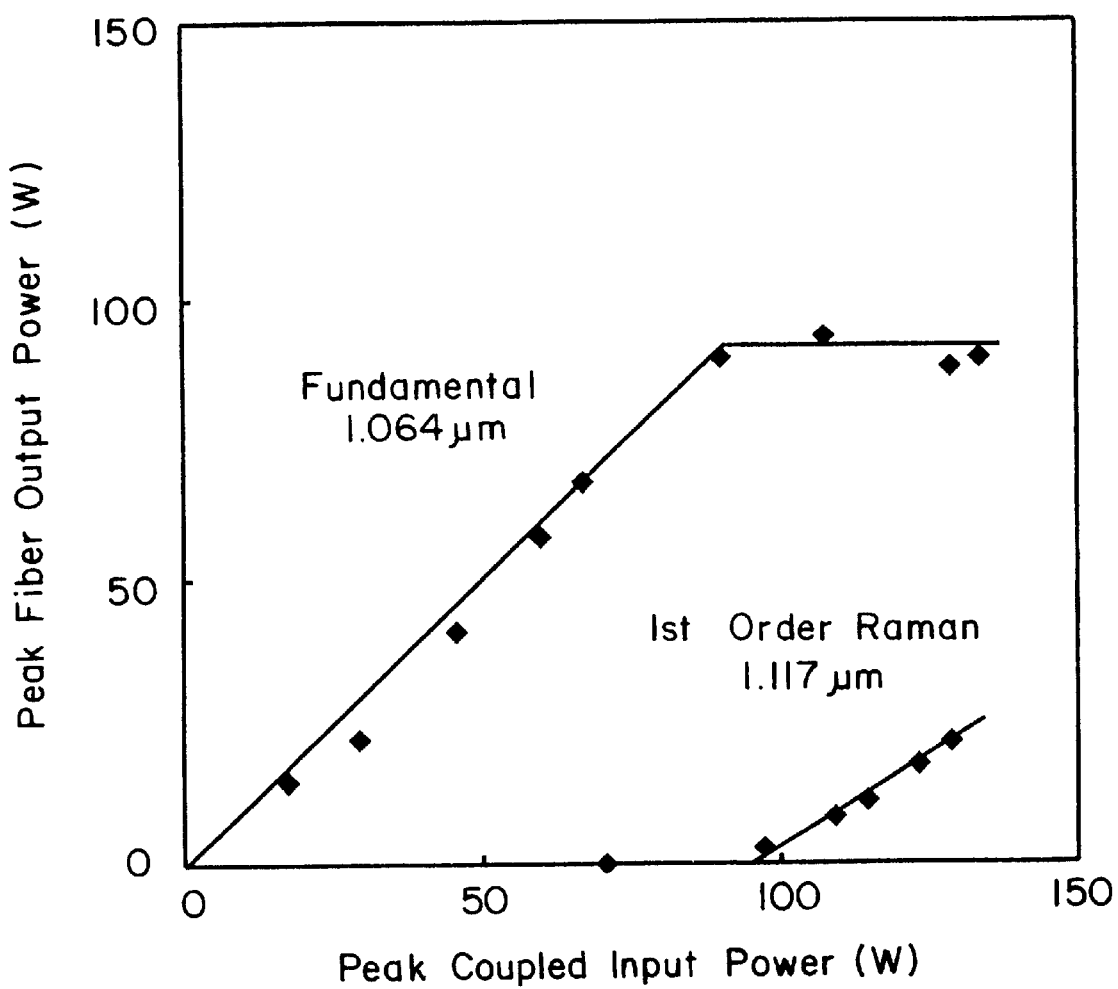
FIG. 4 presents a series of curves illustrating the effects of coupling a laser beam having an input power above the SRS threshold into an optical fiber.
Figure 5:
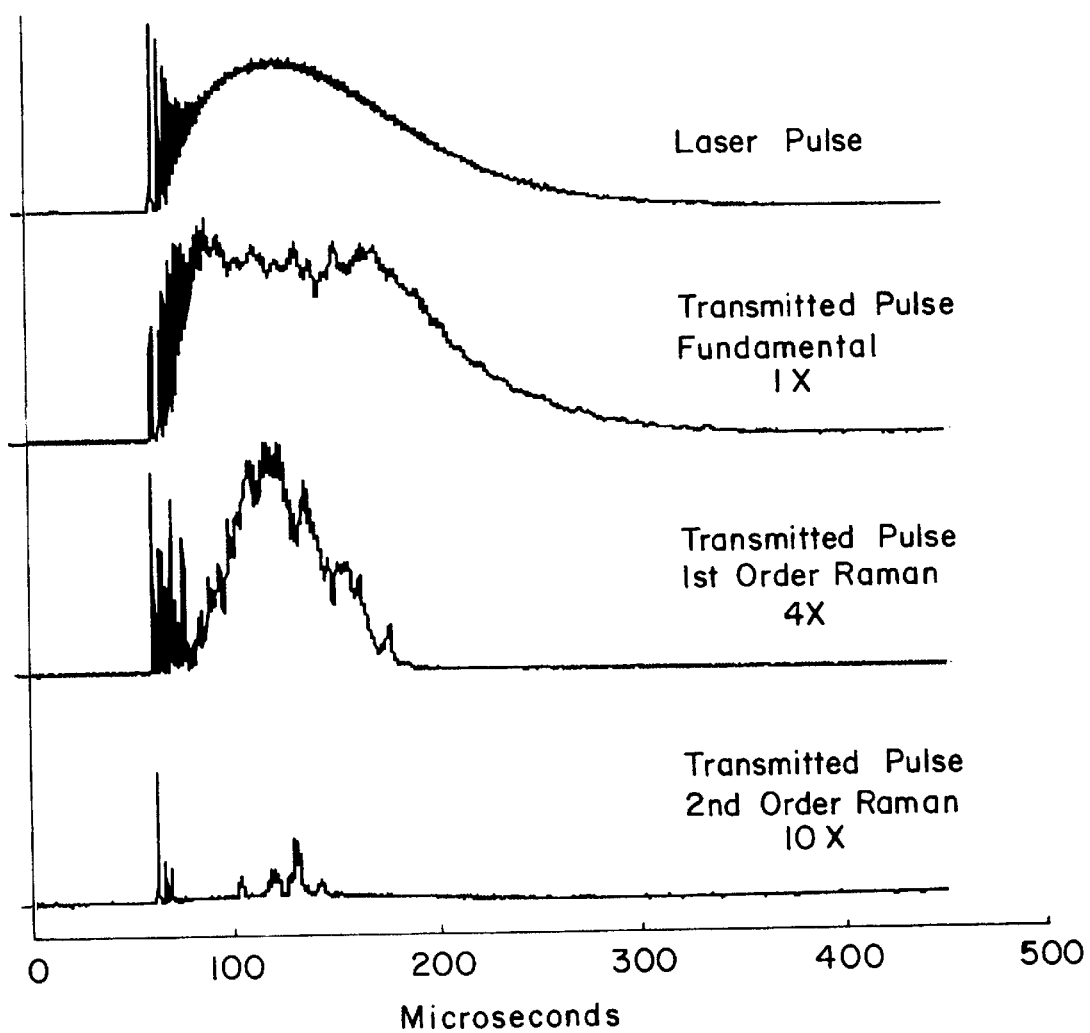
FIG. 5 presents a comparison of an input laser pulse, an amplified laser pulse, a first-order Raman pulse and a second order Raman pulse, looking top to bottom, with respect to identical time scales.
Figure 6:
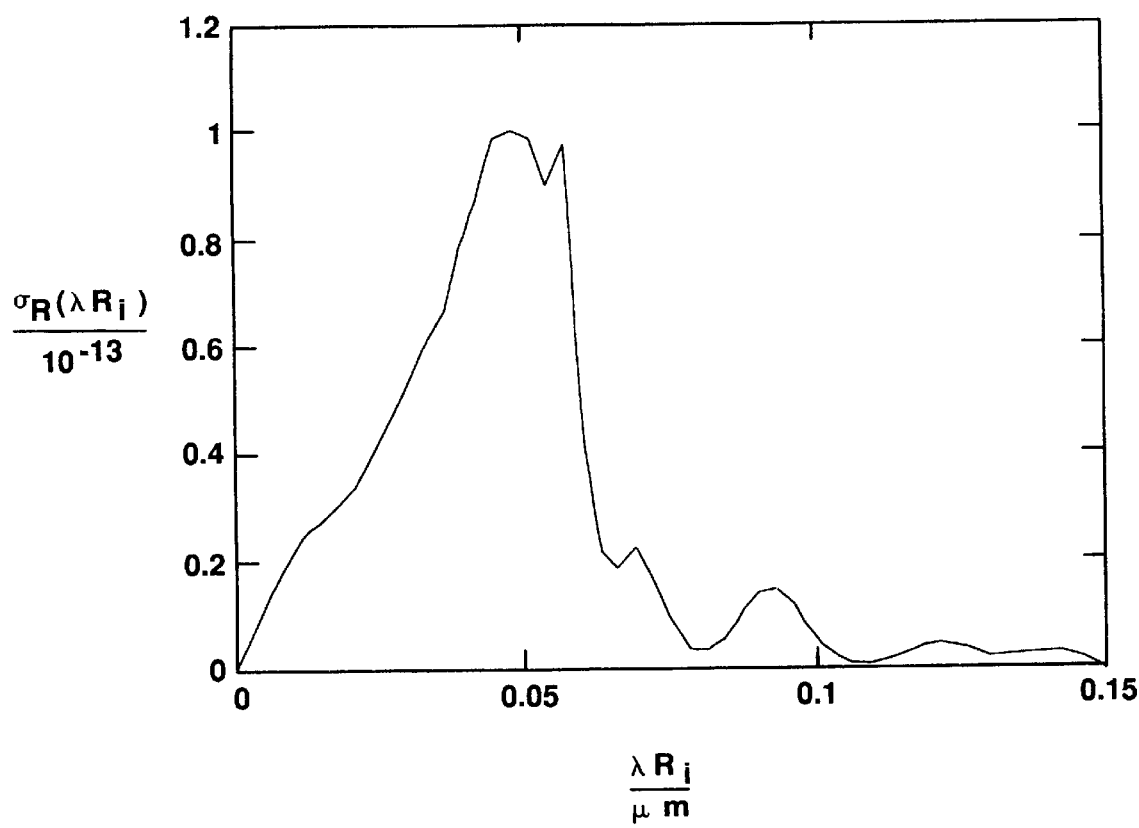
FIG. 6 is a curve depicting the Raman gain in an exemplary optical fiber cable core.
Figure 7:
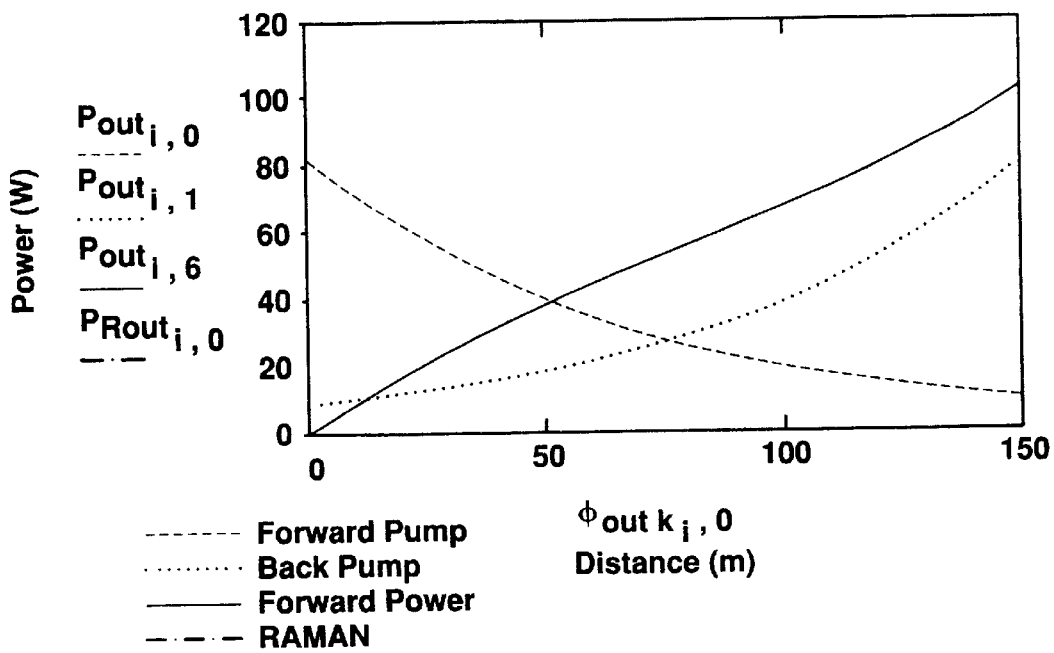
FIGS. 7 and 8 collectively illustrate operation in the gain band of the rare earth dopant used in the fiber amplifier core and Raman gain for relatively short and long optical fiber cables, respectively.
Figure 8:
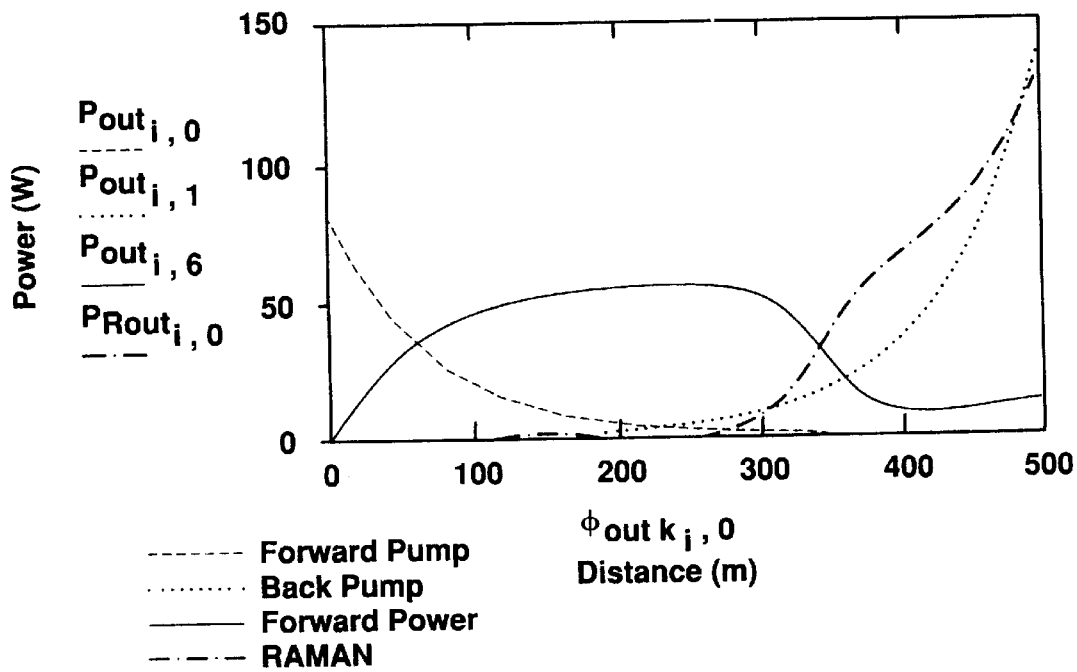

As discussed above, the Raman gain is broadly centered about a wavelength about 53 nm longer than the incoming laser beam's wavelength, depending upon the composition of the fiber core but not the laser beam's wavelength. However, as illustrated in FIGS. 3 and 6, the Raman gain is concentrated in a wavelength region and not in a single wavelength; the Raman laser gain region allows selection of the desired output laser wavelength from any frequency within the Raman gain region. In the exemplary case under discussion, the output Raman laser beam advantageously can be built up from spontaneous Raman scattering, i.e., signal photons inelastically scattered from phonons with a loss of energy and subsequent increase in wavelength. It will be appreciated that it is the stimulated Raman scattering process, i.e., amplification of photons present at the down-shifted wavelength, that makes SRS a problematic parasitic process in the array 200 of FIG. 1. However, it is SRS that enables Raman amplifier designs to cover wavelengths that can not be amplified by conventional rare earth doped amplifiers.

It should be mentioned briefly that a Raman amplifier is not as efficient as the amplifier that pumps it, since energy is lost to phonons and a small amount of the pumping signal is not converted. However, the power loss penalty can be considered a minor cost when compared to the overall wavelength flexibility provided by the phased array Raman laser amplifier according to the present invention. Of course, the high power first Raman signal can induce a second Raman parasitic and so on, as specifically depicted in FIG. 3.

It should also be mentioned that various modifications to the present invention can be made without departing from the present invention. In particular, since the elements in the power amplifier array 400 are nonlinear elements, various design parameters advantageously can be adjusted to tune the phased array Raman laser amplifier to the intended application. For example, it will be appreciated that the onset of SRS advantageously can be controlled by controlling the length of the optical fiber in power amplifier 420 or the cross section of the optical fiber of power amplifier 420, or both. Moreover, as discussed above, variations in the dopant and the material making up the rare earth doped optical fiber advantageously can be used to control the onset of SRS. It will be appreciated that the required gain for the fundamental laser beam in the elements 410 can be determined once the characteristics of the power amplifiers 420 are selected.

In summary, the preferred embodiment according to the present invention is a method of PDT treatment for inducing remission in malignant cells using a phased array Raman laser amplifier composed of all solid state elements to excite a photosensitizer compound present in the targeted cells. The present invention has many desirable features, such as modularity, high power, high efficiency, wavelength diversity, making the phased array Raman laser amplifier desirable over other laser systems having similar operating frequencies in the PDT field.

Although presently preferred embodiments of the present invention have been described in detail hereinabove, it should be clearly understood that many variations and/or modifications of the basic inventive concepts herein taught, which may appear to those skilled in the pertinent art, will still fall within the spirit and scope of the present invention, as defined in the appended claims.

For instance, while the present invention has been illustrated in the context of PDT treatments, the laser system also could be used in other medical procedures requiring excitation of photosensitizer agents as selectively accumulated in certain living tissues, such as in the treatment of plaque build-up and clogging in blood vessels due to arteriosclerosis, age-related macular degeneration (AMD), and the like.

What is claimed is:

1. A method of photodynamic therapy, comprising the steps of:
    contacting tumor cells with a photosensitizer compound;
    irradiating said tumor cells in the presence of said photosensitizer compound with a laser beam at a light wavelength effective to excite said photosensitizer compound to cause cytotoxic effects upon the tumor cells, wherein said laser beam is generated using a phased array Raman laser amplifier including: (a) a beam generator generating a fundamental laser beam and a Raman seed frequency laser beam, and (b) a laser amplifier array forming a diffraction limited output laser beam at the Raman seed frequency by amplifying said fundamental laser beam to a power level corresponding to a Stimulated Raman Scattering (SRS) threshold to thereby pump the SRS process and provide Raman gain to the Raman seed frequency laser beam.

2. The method of photodynamic therapy as recited in claim 1, wherein said light wavelength is in the range of about 500 to about 1600 nm.

3. The method of photodynamic therapy as recited in claim 1, wherein said light wavelength is in the red light spectral range.

4. The method of photodynamic therapy as recited in claim 1, wherein said photosensitizer compound is selected from the group consisting of porphyrins, chlorins, phthalocyanines, naphthalocyanines, carbocyanines, and derivatives thereof.

5. The method of photodynamic therapy as recited in claim 1, wherein said beam generator comprises:
    a fundamental oscillator for producing said fundamental laser beam;
    a Raman oscillator for producing said Raman seed frequency laser beam; and
    a wavelength combiner for combining and applying said fundamental laser beam and said Raman seed frequency laser beam to said laser amplifier array.

6. The method of photodynamic therapy as recited in claim 1, wherein said Raman oscillator is a locked frequency Raman oscillator.

7. The method of photodynamic therapy as recited in claim 1, further comprising using a frequency doubler for doubling the frequency of the diffraction limited output laser beam so as to produce a frequency doubled diffraction limited output laser beam.

8. The method of photodynamic therapy as recited in claim 7, wherein said laser amplifier array comprises:
    a beam splitter receiving said fundamental laser beam and said Raman seed frequency laser beam and generating N secondary fundamental and N Raman seed frequency laser beams;
    N parallel rare earth doped optical fiber sections, each of said optical fiber sections amplifying a respective one of said N secondary fundamental laser beams to thereby produce N tertiary laser beams at the power level corresponding to a Stimulated Raman Scattering (SRS) threshold to thereby pump the SRS process and provide Raman gain to the N Raman seed frequency laser beams to thereby produce N amplified Raman seed frequency laser beams; and
    an optical combiner for receiving at least said N Raman seed frequency laser beams and for generating said diffraction limited output laser beam at the Raman seed frequency;
    wherein N is an integer greater than or equal to 2.

9. The method of photodynamic therapy as recited in claim 8, wherein said laser amplifier array further comprises:
    a beam splitter receiving said fundamental laser beam and said Raman seed frequency laser beam and generating N secondary fundamental and N Raman seed frequency laser beams; and
    N parallel rare earth doped optical fiber sections, each of said optical fiber sections amplifying a respective one of said N secondary fundamental laser beams to thereby produce N tertiary laser beams at the power level corresponding to a Stimulated Raman Scattering (SRS) threshold to thereby pump the SRS process and provide Raman gain to the N Raman seed frequency laser beams to thereby produce N amplified Raman seed frequency laser beams; and
    an optical combiner for receiving at least said N Raman seed frequency laser beams and for generating said diffraction limited output laser beam at the Raman seed frequency;

wherein N is an integer greater than or equal to 2.

10. The method of photodynamic therapy as recited in claim 9, wherein each of said optical fiber sections comprises a doped single mode optical fiber core, and wherein a dopant is selected from a group consisting of Nd, Yb, Yb:Er, Er, Pr, Ho, and a semiconductor material.

11. The method of photodynamic therapy as recited in claim 9, wherein said N optical fiber sections are connected to said combiner by a fiber optic bundle.

12. A method of photodynamic therapy, comprising the steps of:
contacting tumor cells with a photosensitizer compound;
irradiating said tumor cells in the presence of said photosensitizer compound with a laser beam at a light wavelength effective to excite said photosensitizer compound to cause cytotoxic effects upon the tumor cells, wherein said laser beam is generated using a phased array Raman laser amplifier including: (a) first means for generating a fundamental laser beam, (b) second means for generating a Raman seed frequency laser beam, (c) third means for combining said fundamental laser beam and said Raman seed frequency laser beams, (d) fourth means for generating N fundamental laser beams and for generating N Raman seed frequency laser beams responsive to the combined fundamental laser beam and Raman seed frequency laser beams, (e) fifth means for amplifying the power level of each of said N fundamental laser beams to a Stimulated Raman Scattering (SRS) threshold associated with said fifth means to thereby pump the SRS process so as to provide Raman gain for each of said N Raman seed frequency laser beams to thereby produced N amplified Raman seed frequency laser beams, and (f) sixth means for combining said N amplified Raman seed frequency laser beams to thereby produce a diffraction limited output laser beam.

13. The method of photodynamic therapy as recited in claim 12, wherein said sixth means comprises:
seventh means for doubling the frequency of each of said N amplified Raman seed frequency laser beams so as to produce N frequency doubled laser beams; and
eighth means for combining said N frequency doubled laser beams to thereby produce the diffraction limited output laser beam.

14. The method of photodynamic therapy as recited in claim 12, wherein:
said second means comprises means for generating first and second Raman seed frequency laser beams each having a different frequency;
said third means comprises means for combining said fundamental laser beam and said first and second Raman seed frequency laser beams;
said fourth means comprises means for generating N fundamental laser beams and for generating N first and second Raman seed frequency laser beams responsive to the combined fundamental laser beam and first and second Raman seed frequency laser beams; and
said fifth means comprises means for amplifying the power level of each of said N fundamental laser beams to the Stimulated Raman Scattering (SRS) threshold associated with said fifth means to thereby pump the SRS process so as to provide Raman gain for each of said N first and second Raman seed frequency laser beams to thereby produce N amplified Raman seed frequency laser beams at the second Raman seed frequency.

15. A method of photodynamic therapy, comprising the steps of:
contacting tumor cells with a photosensitizer compound;
irradiating said tumor cells in the presence of said photosensitizer compound with a laser beam at a light wavelength effective to excite said photosensitizer compound to cause cytotoxic effects upon the tumor cells, wherein said laser beam is generated using a phased array Raman laser amplifier including (a) a beam generator for generating a fundamental laser beam and a Raman seed frequency laser beam, and (b) a fiber optic laser amplifier for forming a diffraction limited output laser beam at the Raman seed frequency by amplifying the fundamental and Raman seed frequency laser beams by Stimulated Raman Scattering (SRS), in which the use of said phased array Raman laser amplifier comprises the substeps of:
(i) generating a fundamental laser beam;
(ii) generating a Raman seed frequency laser beam;
(iii) generating N fundamental laser beams responsive to said fundamental laser beam;
(iv) generating N Raman seed frequency laser beams responsive to said Raman seed frequency laser beam;
(v) amplifying the power level of each of said N fundamental laser beams to a Stimulated Raman Scattering (SRS) threshold associated with the fiber optic laser amplifier to thereby pump the SRS process so as to provide Raman gain for each of said N Raman seed frequency laser beams to thereby produced N amplified Raman seed frequency laser beams; and
(vi) combining said N amplified Raman seed frequency laser beams to thereby produce the diffraction limited output laser beam.

16. The method for photodynamic therapy as recited in claim 15, wherein said step (vi) comprises the steps of:
doubling the frequency of each of said N amplified Raman seed frequency laser beams so as to produce N frequency doubled laser beams; and
combining said N frequency doubled laser beams to thereby produce a diffraction limited output laser beam.

17. A method of photodynamic therapy using a light source generating a precise output wavelength in a laser amplifier array, comprising the steps of:
contacting tumor cells with a photosensitizer compound;
irradiating said tumor cells in the presence of said photosensitizer compound with a laser beam at a light wavelength effective to excite said photosensitizer compound to cause cytotoxic effects upon the tumor cells, wherein said laser beam is generated using a phased array Raman laser amplifier including (a) a beam generator for generating a fundamental laser beam and a Raman seed frequency laser beam, and (b) a fiber optic laser amplifier for forming a diffraction limited output laser beam at the Raman seed frequency by amplifying the fundamental and Raman seed frequency laser beams by Stimulated Raman Scattering (SRS), in which the use of said phased array Raman laser amplifier
applying a frequency-locked Raman seed frequency laser beam and a fundamental laser beam to the laser amplifier array: and
generating an output laser beam using a Stimulated Raman Scattering (SRS) process whereby the majority of the power of said output laser beam is at the frequency-locked Raman seed frequency.

* * * * *